United States Patent
Groves et al.

(10) Patent No.: US 8,325,061 B2
(45) Date of Patent: Dec. 4, 2012

(54) SYSTEM AND METHOD FOR MOBILE ENVIRONMENTAL MEASUREMENTS AND DISPLAYS

(75) Inventors: Bruce D. Groves, Madison, NJ (US); Thomas P. Carlson, Maplewood, NJ (US)

(73) Assignee: Emilcott Associates, Inc., Chatham, MA (US)

( * ) Notice: Subject to any disclaimer, the term of this patent is extended or adjusted under 35 U.S.C. 154(b) by 487 days.

(21) Appl. No.: 12/683,702

(22) Filed: Jan. 7, 2010

(65) Prior Publication Data

US 2011/0163892 A1 Jul. 7, 2011

(51) Int. Cl.
*G08G 1/00* (2006.01)

(52) U.S. Cl. ............... 340/901; 340/524; 340/573.1; 340/932.2; 340/539.13

(58) Field of Classification Search ........... 340/901, 340/524, 537.1, 932.2, 539.13, 539.2, 572.1, 340/573.3, 540, 57.1; 700/245
See application file for complete search history.

(56) References Cited

U.S. PATENT DOCUMENTS

| | | | |
|---|---|---|---|
| 5,202,661 A | | 4/1993 | Everett, Jr. et al. |
| 5,446,445 A | | 8/1995 | Bloomfield et al. |
| 5,525,882 A | | 6/1996 | Asaka et al. |
| 5,650,770 A | * | 7/1997 | Schlager et al. ........... 340/573.1 |
| 5,652,570 A | * | 7/1997 | Lepkofker ................. 340/573.4 |
| 6,031,454 A | * | 2/2000 | Lovejoy et al. .......... 340/539.29 |
| 6,102,617 A | | 8/2000 | Hampton |
| 6,252,544 B1 | | 6/2001 | Hoffberg |
| 6,646,559 B2 | * | 11/2003 | Smith ......................... 340/601 |
| 7,218,993 B2 | | 5/2007 | Yasukawa et al. |
| 7,222,018 B2 | * | 5/2007 | Uyeki et al. ................. 701/423 |
| 7,245,216 B2 | * | 7/2007 | Burkley et al. ........... 340/539.13 |
| 7,400,974 B2 | * | 7/2008 | Fuchs et al. ................... 701/484 |
| 7,432,806 B2 | * | 10/2008 | Radin ....................... 340/539.13 |
| 7,491,948 B2 | * | 2/2009 | Gordon et al. ............. 250/472.1 |
| 7,492,255 B1 | * | 2/2009 | Morris ......................... 340/541 |
| 7,518,505 B2 | * | 4/2009 | Smith ....................... 340/539.13 |
| 7,545,269 B2 | * | 6/2009 | Craig et al. ............... 340/539.26 |
| 7,620,406 B2 | * | 11/2009 | Nagashima et al. ........ 455/456.1 |
| 7,656,287 B2 | * | 2/2010 | Albert et al. .................. 340/521 |
| 7,675,410 B2 | * | 3/2010 | Aritsuka et al. ........... 340/539.1 |
| 7,710,290 B2 | * | 5/2010 | Johnson ........................ 340/8.1 |
| 7,805,150 B2 | * | 9/2010 | Graham et al. ............ 455/456.3 |
| 8,185,623 B2 | * | 5/2012 | Lewis et al. .................. 709/224 |
| 2001/0009407 A1 | * | 7/2001 | Honda et al. ............. 342/357.09 |
| 2002/0080038 A1 | * | 6/2002 | Smith ........................... 340/601 |
| 2002/0186135 A1 | * | 12/2002 | Wagner ...................... 340/573.1 |
| 2003/0234725 A1 | * | 12/2003 | Lemelson et al. ............ 340/521 |
| 2004/0070515 A1 | * | 4/2004 | Burkley et al. .......... 340/825.49 |
| 2004/0077347 A1 | * | 4/2004 | Lauber et al. ................ 455/428 |
| 2005/0001024 A1 | * | 1/2005 | Kusaka et al. ................ 235/375 |
| 2005/0156715 A1 | * | 7/2005 | Zou et al. ................. 340/426.19 |

(Continued)

*Primary Examiner* — Hoi Lau
(74) *Attorney, Agent, or Firm* — Diehl Servilla LLC

(57) ABSTRACT

An environmental measurement system and method are disclosed. In one aspect of the invention, the system includes a base station having a processor, a plurality of environmental detectors located remotely from the base station that measure one or more environmental conditions that are in communication with the base station to send the measured one or more environmental conditions to the base station and a plurality of user display stations located remotely from the base station that are in communication with the base station and that can display the one or more environmental conditions received from the base station. One or more of the environmental detectors or one or more of the user display stations is mobile. Alternatively, the environmental detectors and the user display stations can both be mobile.

26 Claims, 7 Drawing Sheets

U.S. PATENT DOCUMENTS

| | | |
|---|---|---|
| 2005/0174220 A1* | 8/2005 | Flick .................... 340/426.18 |
| 2006/0015254 A1* | 1/2006 | Smith ............................ 702/3 |
| 2006/0158329 A1* | 7/2006 | Burkley et al. .......... 340/539.13 |
| 2006/0267783 A1* | 11/2006 | Smith ......................... 340/601 |
| 2007/0018806 A1* | 1/2007 | Craig et al. ................. 340/500 |
| 2007/0018807 A1* | 1/2007 | Craig et al. ................. 340/500 |
| 2007/0030156 A1* | 2/2007 | Schlager et al. .......... 340/573.1 |
| 2007/0103292 A1* | 5/2007 | Burkley et al. .......... 340/539.13 |
| 2008/0012701 A1* | 1/2008 | Kass et al. .............. 340/539.11 |
| 2008/0030345 A1* | 2/2008 | Austin et al. ............. 340/572.8 |
| 2008/0036610 A1* | 2/2008 | Hokuf et al. ............. 340/573.3 |
| 2008/0158002 A1* | 7/2008 | Parkinson et al. ....... 340/825.49 |
| 2008/0164984 A1* | 7/2008 | Sheffer ................... 340/426.13 |
| 2008/0167806 A1* | 7/2008 | Wheeler et al. .............. 701/208 |
| 2008/0311882 A1* | 12/2008 | Schlager et al. ........... 455/404.2 |
| 2009/0146846 A1* | 6/2009 | Grossman .................... 340/988 |
| 2009/0160646 A1* | 6/2009 | Mackenzie et al. ........ 340/572.1 |
| 2010/0164713 A1* | 7/2010 | Wedig et al. ............. 340/539.13 |
| 2010/0176952 A1* | 7/2010 | Bajcsy et al. .............. 340/573.1 |
| 2011/0148623 A1* | 6/2011 | Bishop et al. ............ 340/539.13 |
| 2011/0163892 A1* | 7/2011 | Groves et al. ................ 340/901 |

* cited by examiner

Multiple User Display Devices, Both Mobile and Fixed.

Remote Data Download via Intermediate Measurement Stations.

SYSTEM AND METHOD FOR MOBILE ENVIRONMENTAL MEASUREMENTS AND DISPLAYS

BACKGROUND OF THE INVENTION

The present invention relates to environmental measurement and detection systems.

Present environmental measurement and detection systems are typically fixed systems that are established in accordance with pre-conceived ideas about where environmental problems may be. Environmental conditions at locations of interest can, however, vary. Existing environmental measurement and detection systems lack the capability of adjusting to any changing conditions.

Existing environmental measurement and detection systems require manual reconfiguration to address changing issues. Existing environmental measurement and detection systems also lack the ability to provide measurements of personal exposure to environmental conditions.

New environmental measuring and detecting systems are needed to cope with changing conditions and to provide additional capabilities.

SUMMARY OF THE INVENTION

In accordance with an aspect of the present invention, an environmental measurement system is provided. The system includes a base station having a processor and a plurality of environmental detectors located remotely from the base station that measure one or more environmental conditions. The plurality of environmental measurement systems are in communication with the base station to send the measured one or more environmental conditions to the base station. At least one of the plurality of environmental detectors is mobile and has a means for determining its position and for reporting it position to the base station.

The environmental measurement system can also include a plurality of user displays stations located remotely from the base station that are in communication with the base station and that can display the one or more environmental conditions received from the base station. At least one of the plurality of user display stations is mobile.

In accordance with a further aspect of the present invention, an environmental measuring system each of the plurality of user display stations can selectively display information from any of the plurality of environmental detectors.

In the environmental measuring system of the present invention, a plurality of environmental detectors can be mobile and can have a means for determining its position and for reporting it position to the base station.

The means for determining position is a Global Positioning System (GPS). GPS systems and devices are well known, and a wide variety of GPS devices can be used in accordance with the present invention. The means for determining position can also be any other means for determining the position of a device. For example, Cell-ID Network; WiFi Network; Network Triangulation, signal strength-based; Network Triangulation, time-based, which can include either Time Difference of Arrival (TDOA) or Advanced Forward Link Triangulation (AFLT), can also be used.

In accordance with a further aspect of the present invention, the system can include a plurality of user displays stations located remotely from the base station that are in communication with the base station and that can display the one or more environmental conditions received from the base station. At least one of the plurality of user display stations can be mobile.

In accordance with another aspect of the present invention, all communications with the base station are wireless communications.

In the environmental measuring system of the present invention, the mobile environmental detector can report its position and data in a number of different ways. It can report its position to the base station on a periodic basis, so reports are sent automatically once during a period. The reporting by the environmental detector to the base station can be made either while the mobile environmental detector is moving or stationary. Additionally, the reporting by the environmental detector to the base station can also be made when the base station queries the environmental detector. Any combination of these reporting procedures can be used by any of the environmental detectors or by any of the user display devices.

The environmental measuring system of the present invention can include a secondary environmental detector located remotely from the base station that measures one or more environmental conditions and that is in communication with one of the plurality of environmental detectors which provides information from the secondary environmental detector to the base station. That secondary environmental detector can be mobile.

The environmental measuring system, in accordance with another aspect of the present invention, can include a plurality of secondary environmental detectors located remotely from the base station that measure one or more environmental conditions, each of the plurality of secondary environmental detectors being in communication with one of the plurality of environmental detectors which provides information from the secondary environmental detector to the base station.

The mobile environmental detectors can be adapted to be worn by a person. In this case they act as a personal exposure detector. The mobile environmental detectors can also be adapted to be mounted on vehicles, such as trucks or other excavating equipment, to monitor the environmental conditions in the vicinity of such vehicles and/or conditions created by such vehicles. The mobile environmental detectors can also include wheels, rollers or treads; or tracks or rails; or other means of controlled motion, for example a cable suspension system and movement can be robotically controlled. Additionally, the base station can issue command signals to the mobile environmental detector to control movement of the mobile environmental detector, and to start and stop the measurement operation of the detector.

In accordance with another aspect of the present invention, an environmental measurement system includes a base station having a processor, a plurality of environmental detectors located remotely from the base station that measure one or more environmental conditions that are in communication with the base station to send the measured one or more environmental conditions to the base station and a plurality of user display stations located remotely from the base station that are in communication with the base station and that can display the one or more environmental conditions received from the base station, wherein one of the plurality of user display stations is mobile. Additional user display stations can also be mobile and one or more of the plurality of environmental detectors can also be mobile.

DRAWINGS

DESCRIPTION

Figure 1:
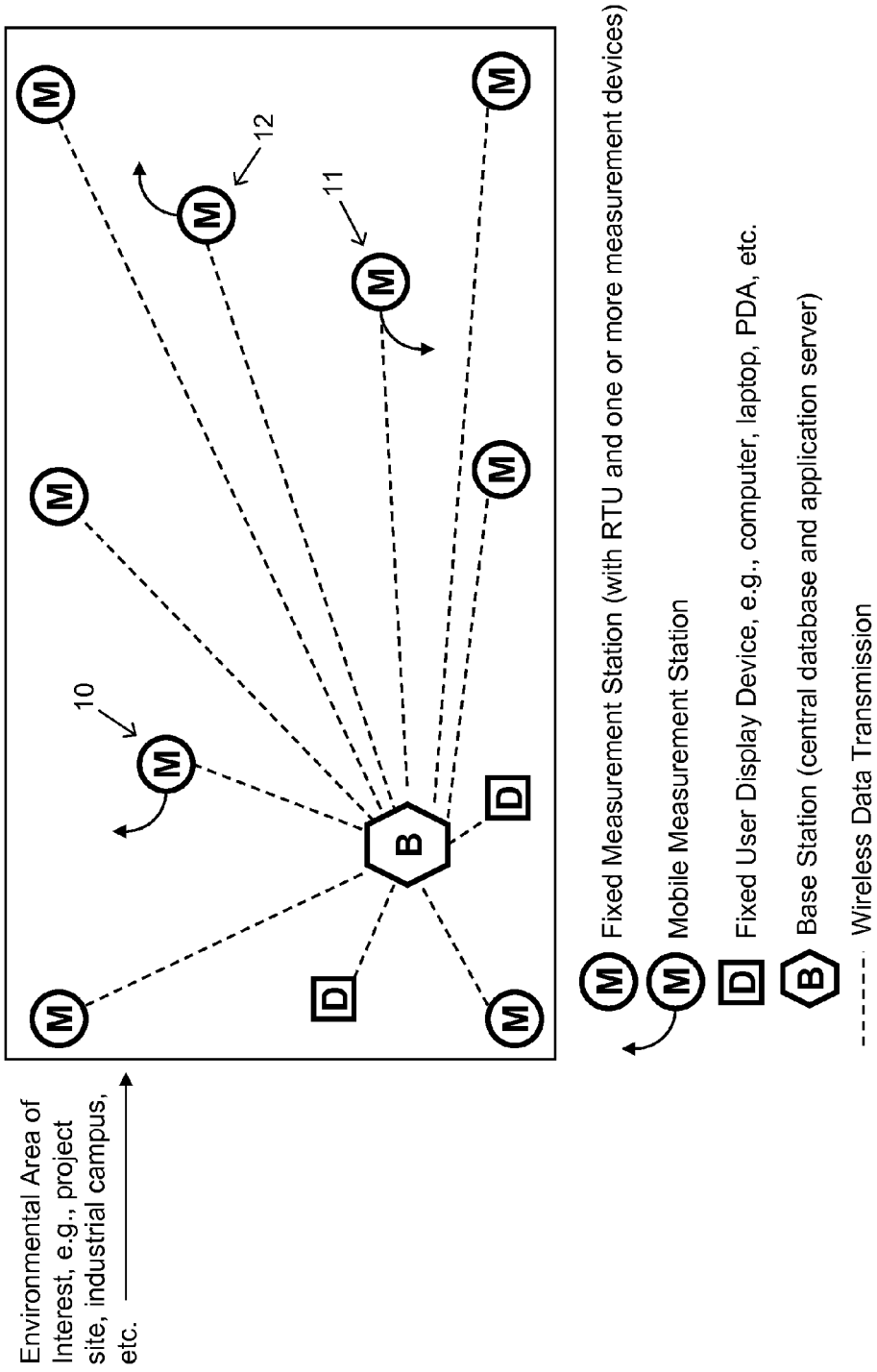
FIG. 1 illustrates an environmental measurement system in accordance with an aspect of the present invention having a plurality of measurement stations that are both mobile and fixed.

An environmental measuring system in accordance with one aspect of the present invention on mobile devices includes, but is not limited to, a number of components. It can include a network of environmental detectors, located in physical housings known as Measurement Stations. The network may, for example, be positioned inside buildings; within an industrial campus; across an industrial, construction, demolition or other project site; surrounding a site of interest for emergency response and/or homeland security purposes; in a wide-ranging urban, rural and/or wilderness area where environmental measurements are of interest.

Each Measurement Station can have one or more environmental detectors; a computer control unit, also known as a Remote Terminal Unit (RTU), that gathers, stores and prepares data for transmission to the Base Station; and a modem, either wireless or hard-wired, to transmit data to the Base Station, wherein such transmission may be directly to the Base Station or via an intermediate measurement station. The types of environmental measurements could include, but are not limited to, airborne particulate concentrations; concentrations of various gases and vapors; noise levels; vibration levels, in soil and/or structures; radiation levels; meteorological data, e.g., temperature, humidity, wind speed, wind direction, accumulated precipitation; video images; location coordinates from GPS or other location-identifying techniques.

The system also includes a Base Station, including a computer database, to store and organize the environmental data readings collected from the Measurement Stations; and a suite of computer applications to analyze, display and report the environmental data to users. Such applications include (but are not limited to): tabular views of environmental measurements with corresponding location coordinates and timestamps; map view of the same; interpolated maps presenting the data as contour diagrams; maps correlating wind speed and direction with environmental data; alerts and alarms as they occur in real-time; time-scale plots of specific measurements.

The system of the present invention can also include one or more User Display Devices. Such devices may be, for example, a personal computer, a laptop, a personal digital assistant (PDA), etc. The User Display Device is connected via network(s) to the Base Station, and is configured with software applications that can present information to users in the form of mapping displays, data tables, audible and visual alerts and alarms, notifications and instructions, summary reports, etc.

Each Measurement Station can have the capability to be configured with a GPS device or other means of real-time location-identification to report its location to the RTU. The RTU can report this position information, along with the measurements taken of the environmental conditions surrounding the Measurement Station, to the Base Station for use in the suite of user-applications.

The RTU can serve as an intermediate database prior to transmission of data to the Base Station. For each environmental sampling measurement, the RTU will provide associated timestamp and location coordinates for transmission to the Base Station.

Each User Display Device can also be configured with a GPS device or other means of real-time location-identification to report its location to the Base Station for use in the suite of user-applications.

Mobile Measurement Stations

In accordance with one aspect of the present invention, one or more of the Measurement Stations is mobile. The mobile Measurement Station can be a fully equipped station as described above. It can also be a version with reduced capabilities to increase the mobility of the Measurement Station.

In accordance with an aspect of the present invention, within a network such as the one just described, one or more of the environmental Measurement Stations are mobile and equipped with a GPS device or other means of real-time location-identification. Among the benefits of this arrangement would be to enable an environmental measurement network to better investigate abnormal and/or changing environmental conditions; to overcome obstacles to wireless data transmission; and to cover a wide range of area efficiently, with fewer detectors. A system having these capabilities in accordance with one aspect of the present invention is shown schematically in FIG. 1.

Referring to FIG. 1, the base station B is in communication with a plurality of Measurement Stations M. Some of the Measurement Stations 10 to 12 are mobile. The base station B is also in communication with a User Display D. All of the Measurement Stations M and the User Display D are remotely located from the base station B in an area to be environmentally investigated. The communications between the Measurement Stations M, the User Display D and the base station B are typically, but not necessarily, wireless.

The mobile Measurement Station M can be adapted to be worn by a person. For example, they can be provided with a shoulder harness, belt-mounted pouch, or other personal mounting systems. In this case, the mobile Measurement Station moves with a person. It can therefore serve as a device to measure personal exposure to various environmental conditions.

The mobile Measurement Station can also be adapted to be located on vehicles. For example, they could have a mounting bracket to be mounted on construction equipment operating in the course of normal work, or on cars, trucks, mobile carts or other vehicles normally travelling in or deliberately roaming an area of interest across the network-site.

The Measurement Stations can also be located on mobile robotic devices. These robotic devices are remotely-controlled surface vehicles and/or aircraft, or fixed-route systems within buildings or industrial sites. They can be controlled locally at the robotic device or they can be controlled by the base station B.

Measurement data can be collected from the Measurement Stations in real-time, and either transmitted in real-time to a Base Station computer for analysis, or retained at the measurement station for later download to the Base Station. The reporting from the Measurement Station to the Base Station can be performed on a selectable periodic basis. The Base Station can provide the period to the Measurement Station. Alternatively, the Measurement Station can report its environmental data when one or more parameters exceed a preset value and/or when any one of various previously specified triggering events occur within the system. Further, the Measurement Station can report to the Base Station while moving or stationary. Alternatively, the Measurement Station can report its position to the Base Station when queried by the Base Station. The reporting is performed by a means for reporting which can be a wired transmitter, a wireless transmitter, a radio, a phone line, a computer line such as a modem or any other transmission device. The Measurement Station can also include a receiver to receive instructions from the Base Station. For example, such instructions could start or stop another monitoring device in the system, or could provide instructions and/or an alarm to the person wearing the mobile station or to the person operating a vehicle equipped with a mobile station.

Mobile User Display Devices

In accordance with further aspects of the present invention, one or more of the User Display Devices, such as a PDA by way of example only, are mobile and equipped with a GPS device or other means of real-time location-identification, such as the ones previously mentioned. This would enable the Base Station to track the location of the users as they move within an environmental measurement network.

Figure 2:
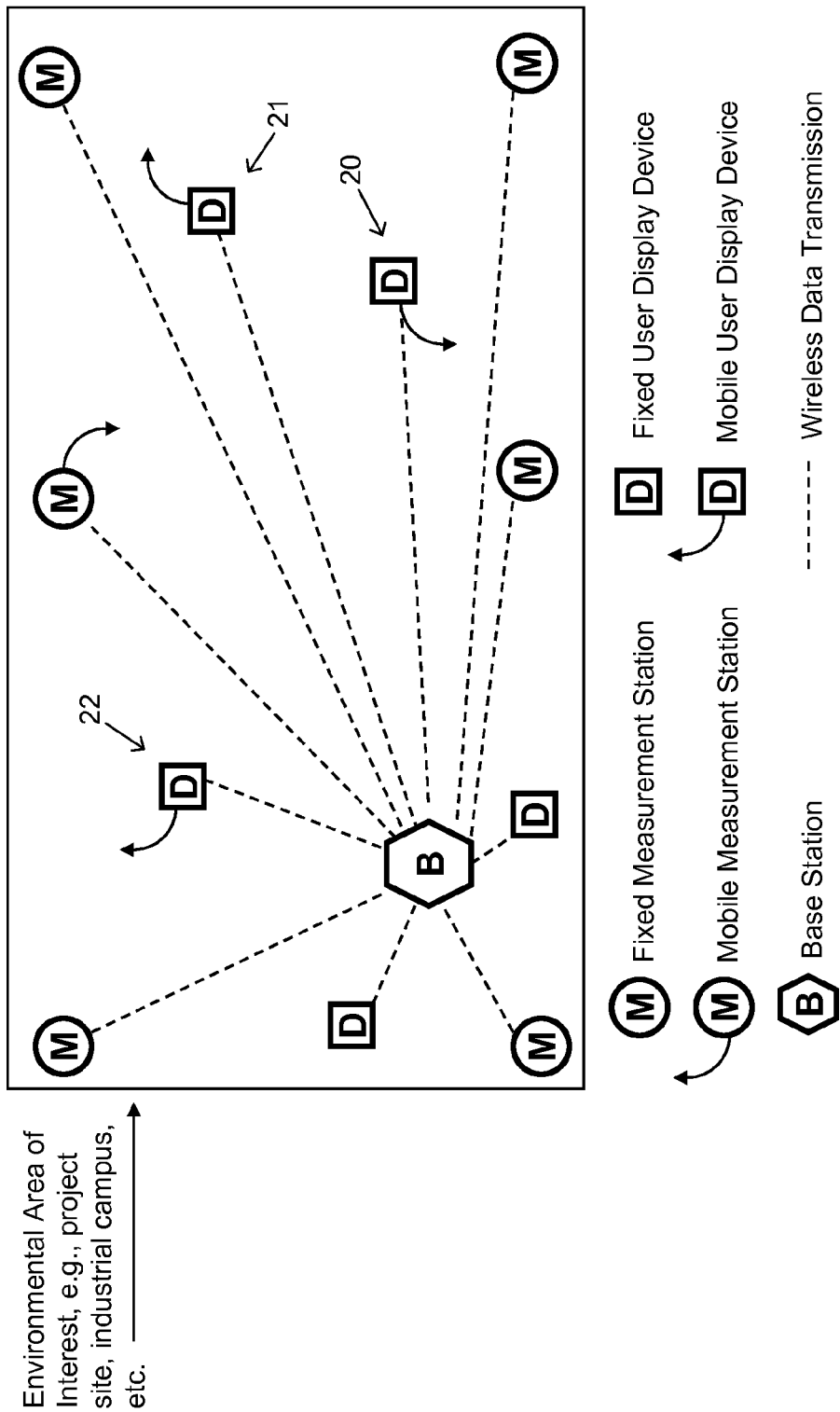
FIG. 2 illustrates an environmental measurement system in accordance with another aspect of the present invention having a plurality of user display devices that are both mobile and fixed.

This aspect of the invention is shown schematically in FIG. 2. User Display Devices 20 to 22 are PDAs or other mobile display devices that are equipped with a GPS device. The GPS device determines the position of the User Display Device and reports it to the Base Station B. The reporting can be periodic, with the period set by the Base Station. Alternatively, the mobile display device can report its environmental data when one or more parameters exceed a preset value and/or when any one of various previously specified triggering events occur within the system. The reporting can be done while the User Display Device is moving or stationary. The User Display Device determines whether it is in motion by analyzing GPS information and then reports the position information to the Base Station B. Alternately, the reporting can be done when the Base Station B queries the User Display Device D. The reporting is performed by a means for reporting which can be a wired transmitter, a wireless transmitter, a radio, a phone line, a computer line such as a modem or any other transmission device. The Measurement Station can also include a receiver to receive instructions from the Base Station.

In accordance with one aspect of the present invention, a Base Station B computer application could compare the location of a portable User Display Device with the network's measurement stations and present a map view of environmental readings interpolated for the location of the display device. A user could move within an environmental measurement network and be made aware of his location with respect to measurement stations and thus to the environmental measurements themselves.

Base Station B applications compile and produce a record of environmental readings over time, including associated location coordinates, thus allowing a portable User Display Device to function as a personal exposure assessment device insofar as the relevant environmental measurements and coordinates could be inferred from interpolation of data from the Measurement Stations. The gathering of such environmental data could occur in real-time, or be downloaded in batches, or some combination, depending on the specific needs of a given exposure assessment exercise.

In accordance with another aspect of the present invention, Base Station B applications analyze environmental conditions across the network, then provide instructions, notifications, warnings, etc. to a user carrying a PDA or other mobile User Display Device. Such instructions, etc. could be made specific to the geographic location of the user within an environmental measurement network.

Combined Mobile Measurement Stations and User Display Devices

In accordance with another aspect of the present invention, within a network, mobile devices are provided that combine the features of a Measurement Station and a User Display Device. This would enable a hybrid capability of the techniques described above.

Figure 3:
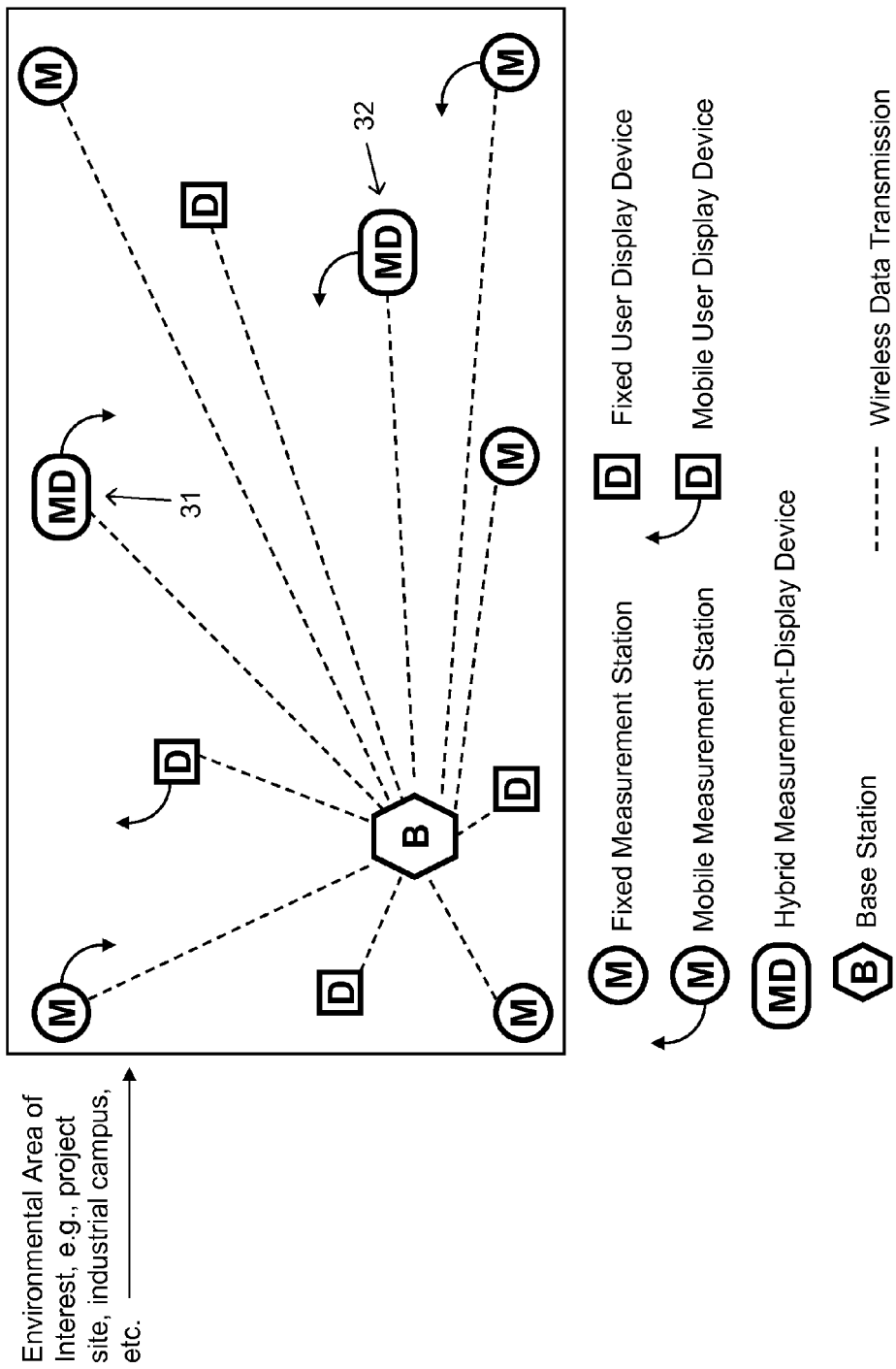
FIG. 3 illustrates environmental measurement system in accordance with a further aspect of the present invention having a plurality of mobile measurement stations and a plurality of user display devices.

This is shown schematically in FIG. 3. Hybrid Measurement-Display Devices 31 and 32 have the capabilities and features of both the mobile measurement devices and mobile display devices, described above. Each such device would have an RTU and one or more measurement devices. Each such device would also have a user display capability as needed for the specific application or project, e.g., graphical displays, audible or visual alarms, text messages, etc. The hybrid devices 31 and 32 include a GPS location device and means for communicating position to the base station B.

These devices could be made sufficiently small and lightweight as to be conveniently carried by a person while performing work duties. Such hybrid devices could be configured as two components of hardware, for example to separate the measurement and display functions when carried by a person. In this instance, the two components could be connected by a data cable or by a local wireless connection such as Bluetooth. Alternatively, for example, such devices could be configured into equipment suitable for mobility in or on vehicles.

Base Station applications could analyze environmental conditions across the network, then provide instructions, notifications, warnings, etc. to a user carrying a PDA or other mobile User Display Device. Such instructions, etc. could be made specific to the geographic location of the user within an environmental measurement network.

Such devices could function as true personal exposure devices because they could record environmental measurements directly. This would enhance the capabilities described above, with respect to compiling, analyzing and displaying such environmental data, either in real-time or be batch downloads.

Base Station and/or RTU applications could analyze environmental conditions across the network or portion thereof, then provide instructions, notifications, warnings, etc. to a user carrying the hybrid measurement/display device. Such instructions, etc. could be made specific to the geographic location of the user within an environmental measurement network.

Remote Data Download

In accordance with another aspect of the present invention, the data-gathering function of the Base Station could be shared with one or more of the RTUs in a network, and such RTUs could later transmit or download their measurement data to the Base Station. This aspect of the present invention is shown schematically in FIG. 4.

Figure 4:
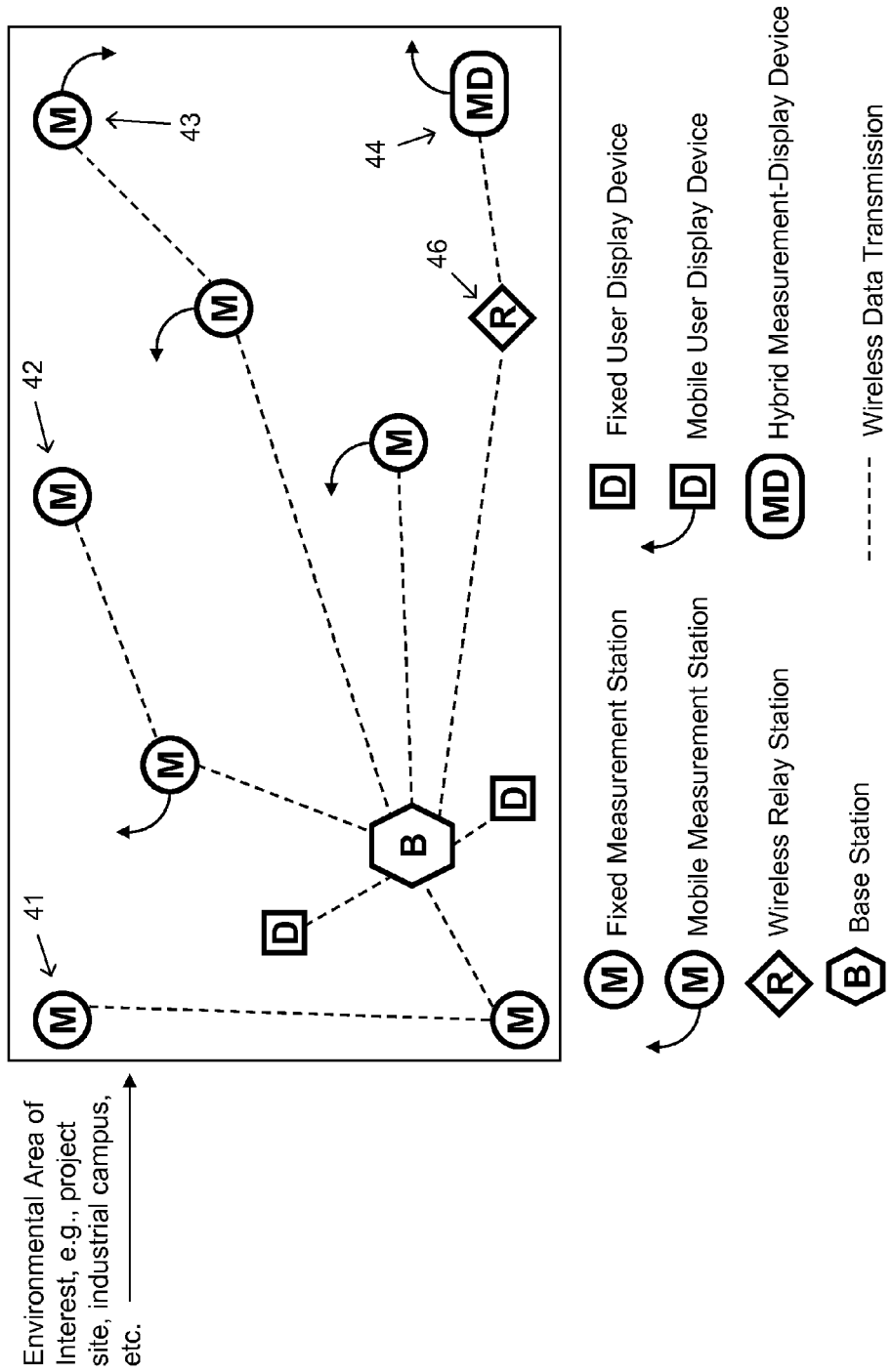
FIG. 4 illustrates environmental measurement system in accordance with a further aspect of the present invention having a plurality of mobile measurement stations and a plurality of user display devices wherein remote data is downloaded via intermediate measurement stations or directly to the base station.

In the system illustrated in FIG. 4, secondary Measurement Stations 41 to 44 are provided. These secondary Measurement Stations 41 to 44 communicate with intermediate Measurement Stations, as illustrated. The information sent can include the environmental conditions measured by the secondary Measurement Stations 41 to 44. If the secondary Measurement Stations are mobile, such as secondary Measurement Stations 43 and 44, then position from a GPS instrument located on such secondary Measurement Stations is also reported to the intermediate Measurement Station. If the secondary Measurement Station is a hybrid Measurement-Display device, as described above, it has the communication capabilities of the other Measurement Stations and also the display capabilities similar to the other User Display devices. In all such instances, the intermediate Measurement Station then communicates the information—environmental conditions and perhaps position information—to the Base Station B.

In accordance with another aspect of the present invention, the intermediate communication station can be a Wireless Relay Station with no environmental measurement capability, but configured solely for the purpose of transmitting environmental and other data from the measurement stations to the base station. This is shown schematically in FIG. 4. In the system illustrated in FIG. 4, Relay Station 46 communicates with both the Base Station B and secondary Measurement Station 44.

This arrangement allows data collection to continue when the Base Station is out of communication with some or all of the measurement stations, is not operational for any reason, or has temporarily been removed from the site for security or other operational reasons.

Such RTUs could be in one or more mobile measurement stations in a network. As such devices roam across the network, they could collect data from other environmental field stations, and later download this data to the Base Station database. This would facilitate large-scale networks where wireless (radio) transmission of data is impractical and/or unreliable.

Alternatively, such RTUs could be independent of the environmental measurement stations, be configured with location-identification technology, and be made mobile. This would allow the roaming data-gathering capability, described above, to be performed by other personnel and/or vehicles than those involved with environmental measurement.

Alternatively, such RTUs, or equivalent processors, could be integrated portable User Display Devices D so as to implement the roaming data download capability with the portable display device.

Roaming (portable) RTUs could transmit data either directly with the Base Station, as described above, or via other RTUs functioning as relay stations within the environmental measurement network.

As describe above, the geographic location of environmental measuring devices could be tracked using Global Positioning System (GPS) or other established location-identifying technologies that are located on the environmental measuring devices. This would enable distinctive and sophisticated environmental mapping applications by integrating environmental and positional measurements from one or more mobile measurement stations. Mobility could be provided by attaching measurement stations to vehicles, people and/or unmanned robotic devices. Such measurements could be combined with similar measurements from fixed stations. Measurement data could be collected in real-time, and either transmitted in real-time to a Base Station computer for analysis, or retained at the measurement station for later download to the Base Station. These measurements could be made in support of perimeter monitoring, personal exposure monitoring and other types of environmental, health and safety data-gathering.

The mapping analyses produced by the Base Station computer could be displayed on mobile computing devices such as PDAs and laptops. These devices could also be tracked with GPS or other location-identifying technologies, and could thus be enabled to dynamically show the user's location within the area of interest where environmental measurements are being taken. The environmental and positional measurements, transmission of data to the Base Station, subsequent analysis, and transmission of displays to users' computing devices could all be done in real-time or near real-time.

In accordance with a further aspect of the present invention, each mobile User Display Device includes a GPS unit and a communication system that allows communications with the Base Station B. These User Display Devices not only receive communications from the Base Station B with information that can be displayed on the User Display Devices, they communicate their positions as determined by the GPS unit back to the Base Station B. These communications are time stamped as well so that the Base Station B can determine where a User Display Device has been at any time.

These User Display Devices can be adapted to be worn or carried by a person, such as with shoulder straps, on belts or with handles. The Base Station B receives measurements of environment conditions from all Measurement Stations in the system. These measurements of environmental conditions are time stamped and the position of the Measurement Stations are either known to the Base Station B or reported through wireless communications to the Base Station B, so that the Base Station B is able to compile a picture of the environmental conditions at any location and at any time.

By comparing the movement (time and location) of a User Display Device through the location being measured to the measured environmental conditions at those locations and times, the processors in the Base Station B can determine a spectrum of exposures to various environmental pollutants to the individual wearing the User Display Device. This information can be downloaded to the User Display Device for display. Alternatively, if any exposures are determined to exceed a limit, the Base Station B can issue an alarm, which can be sent to the User Display Device for creating an alarm display, an alarm sound or both.

Wherever a GPS device is mentioned, any of the previously mentioned position location devices, systems or methods can be used.

Figure 5:
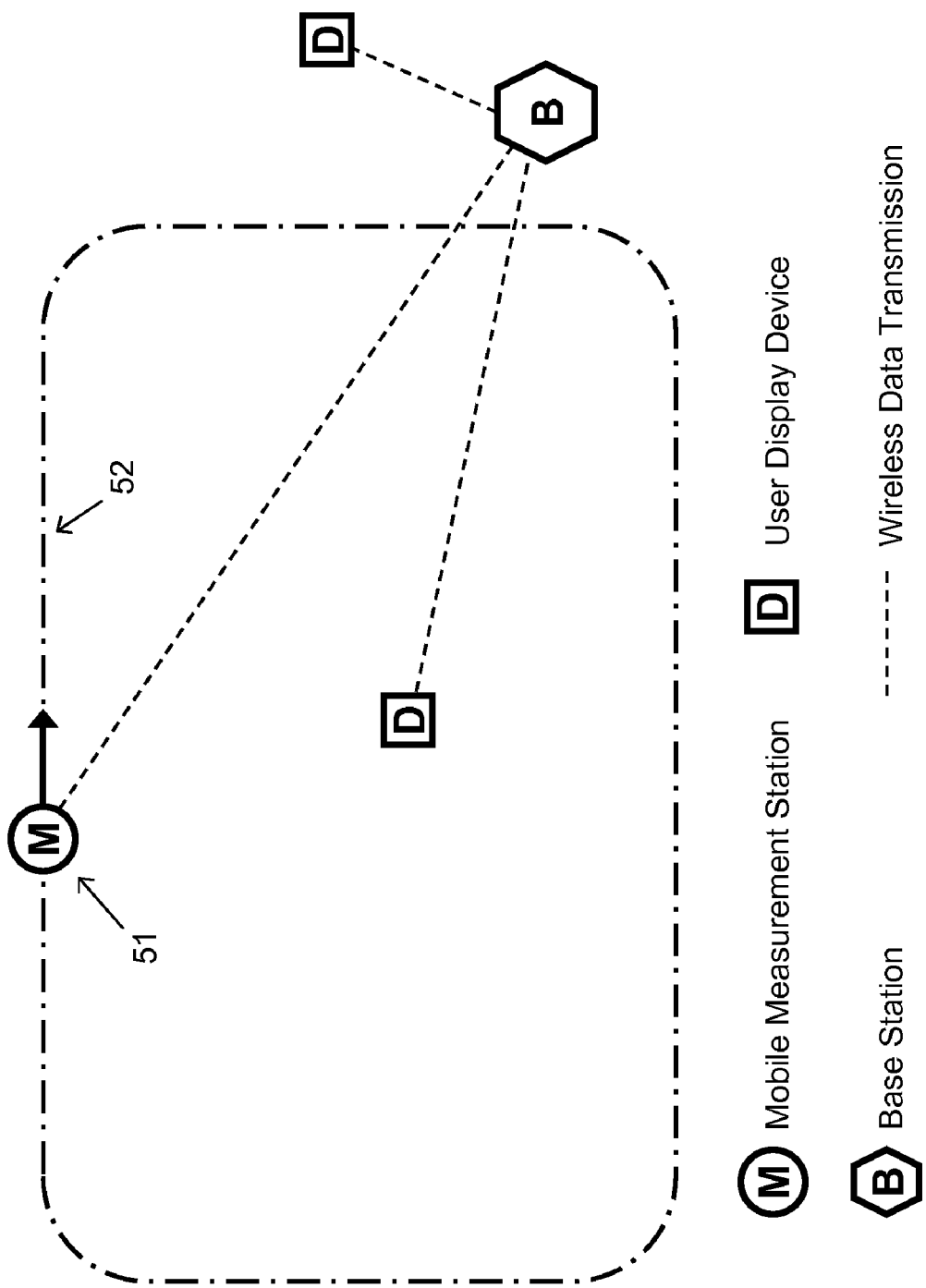
FIGS. 5 to 6 illustrate perimeter monitoring systems in accordance with various aspects of the present invention.

FIG. 5 shows a perimeter monitoring system in accordance with one aspect of the present invention. The perimeter of the system is delineated by a line 52 shown in FIG. 5. The line can consist of means of moving an environmental detector 51, which has been previously described. Thus, the line 52 can be treads; tracks, rails or a cable suspension system or the like. The line 52 can also be a roadway or a path or the like. The environmental detector 51 can include rollers, wheels or the like to enable the movement of the environmental detector 51. The environmental detector 51 communicates wirelessly with a base station B, as previously described. The base station B sends control signals to the environmental detector 51 to move along the line 52. By issuing appropriate start and stop signals for the environmental detector 51, the environmental detector 51 can move along the entire line 52 to cover the entire established perimeter with a single environmental detector 51. Thus, an environmental perimeter monitoring system can be implemented with a single environmental detector or RTU in accordance with an aspect of the present invention. The environmental detector 51 includes a GPS device and reports its position information to the base station B, as previously described.

Additional environmental detectors can be added to the track 52 (or whatever other device is used to control motion of the detector 51 as needed. Thus if a large perimeter is to be monitored in a time frame where motion around the track 52 cannot accommodate the monitoring requirements, additional environmental detectors can be added.

Figure 6:
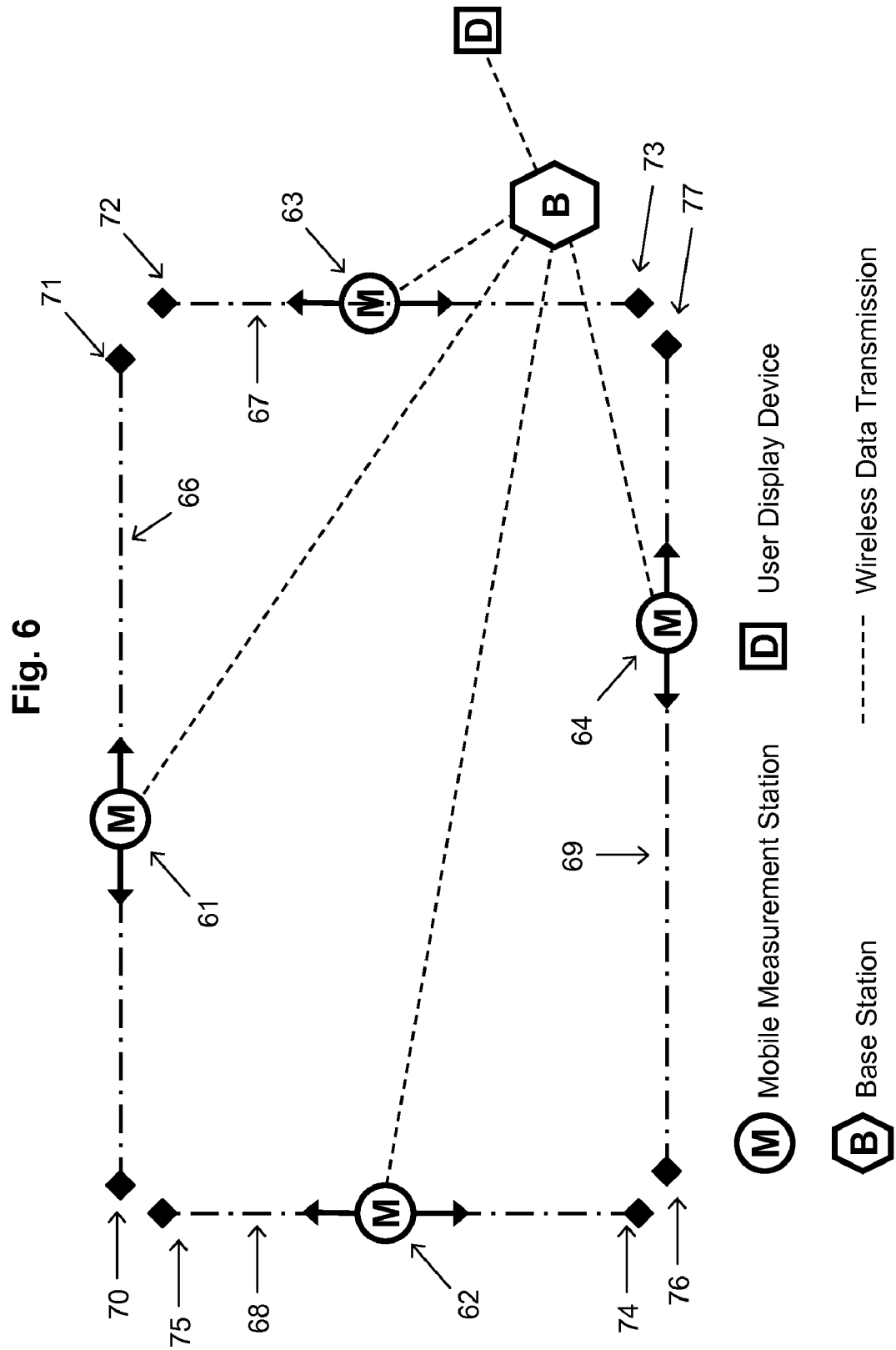

FIG. 6 illustrates another perimeter monitoring system in accordance with another aspect of the present invention. In the perimeter monitoring system of FIG. 6, four tracks are 66, 67, 68 and 69 are provided. Track 66 runs between perimeter point 70 and perimeter point 71. Track 67 runs between perimeter point 72 and perimeter point 73. Track 68 runs between perimeter point 74 and perimeter point 75. Track 69 runs between perimeter point 76 and perimeter point 77. As before, the tracks 66, 67, 68 and 69 can be treads; rails or a cable suspension system or the like. In FIG. 6, mobile environmental detectors 61, 62, 63 and 64 move along the designated tracks or treads or the like. The items 66, 67, 68 and 69 can also be a roadway or a path or the like, as previously mentioned. The environmental detectors 61 to 64 can move in pre-determined paths established by internal programs, or they can move in accordance with programming from the base station B. A user display device D, previously described, can also be provided and can communicate with the base station B.

In accordance with another aspect of the present invention, the mobile environmental detectors shown in FIGS. 5 and 6 can be provided with wheels and a means for driving the wheels and can move along the line 52 in FIG. 5 or along the tracks 66, 67, 68 and 69 in FIG. 6. In this case, the environmental detector can either be programmed to move along the lines or tracks. Alternatively, the environmental detector can transmit its position as determined by a GPS device and a time stamp to the base station B and the base station B can determine appropriate controls to send to the mobile environmental detector to control movement of the environmental detector along a desired route. For example, the environmental detector 51 in FIG. 5 can be programmed, either internally or by the base station B, to move along the line 52 without any track or other device. Similarly, the environmental detectors 61, 62, 63 and 64 can be programmed, either internally or via the base station B, to move along lines between points 70 and 71, 72 and 73, 74 and 75 and 76 and 77, respectively, without any tracks. Thus, in accordance with another aspect of the present invention, the mobile environmental detector can be programmed to move along a path or a roadway which does not guide the direction of the mobile environmental detector. Of course, any perimeter can be so designated.

Also, if the programming is accomplished by the base station B and movement instructions are transmitted from the base station B to the mobile environmental detectors, then the perimeter of the environmental monitoring system can be changed. Thus, if an abnormality is detected by one or more of the environmental detectors, then the base station B can change the path that one or more of the environmental detectors travels on to redefine the perimeter to monitor new points of interest.

Figure 7:
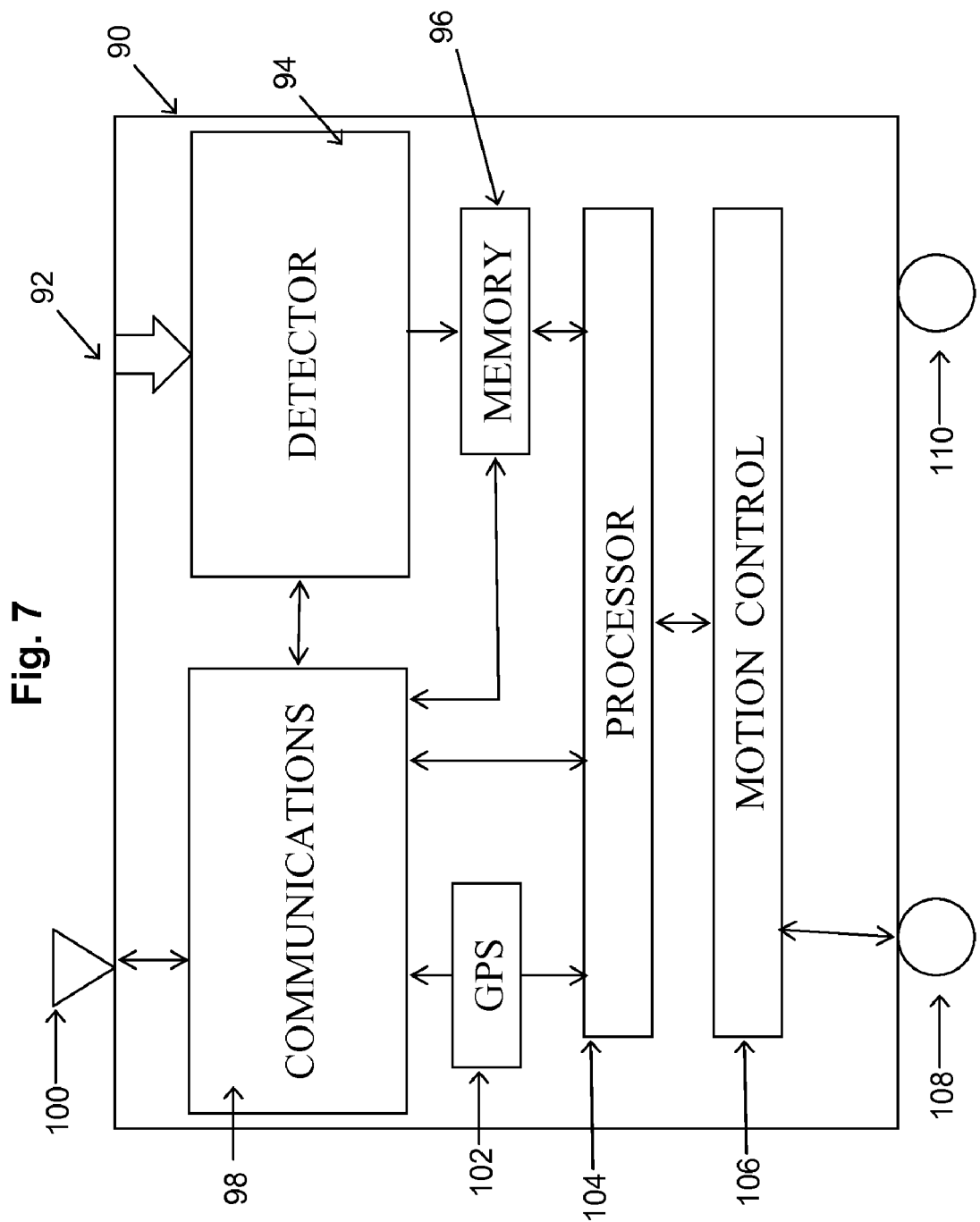
FIG. 7 illustrates a block diagram of a mobile environmental detector in accordance with one aspect of the present invention.

FIG. 7 illustrates a mobile environmental detector 90 in accordance with an aspect of the present invention. The detector 90 includes a port 92, a detection apparatus 94 designed to monitor one or more of a wide variety of environmental conditions, a memory 96, a communication circuit 98, an antenna 100, a GPS device 102, a processor circuit 104, a motion control circuit 106 and two wheels 108 and 110. The detector 94 can be any number of devices and it monitors a selected environmental condition through the port 92. The results of the detection can be stored in memory 96. The results can also be transmitted to the communication circuit 98 where they can be wirelessly transmitted through the antenna 102 to a base station B or to another mobile environmental detector or to a mobile user display device or to a mobile hybrid device previously described.

The memory 96 is also connected to the communication circuit 98 and to the processor circuit 104. The memory 96 is used by these components of the mobile environmental detector as needed.

The GPS device 102 detects the position of the environmental detector 90. That position can be reported to the communications circuit 98 which includes that information in transmissions to the base station B or elsewhere as described in this patent application. The GPS information can also be provided to the processor circuit 104. In cases where the movement programming is internal to the environmental detector 90, the processor circuit 104 uses the position information to provide controls to the motion control circuit 106 which controls one or more motors to turn the wheels 108 and/or 110. If other means to move the mobile environmental detector 90 are utilized, then the motion control circuit 106 provides the control signals necessary to the apparatus used to move the mobile environmental detector 90.

The processor circuit 104 also produces timing information (e.g. time of day, date etc.) that can be transmitted to the communications circuit 98. The communications circuit 98, in accordance with an aspect of the present invention, packages the timing information with position information that is transmitted to the base station B.

As previously described, the base station B can use the position information and/or the timing information it receives from a mobile environmental detector 90 to generate control signals to control movement of the environmental detector 90. In this case, the base station B generates a control signal based on position and timing information and transmits it to the environmental detector 90. The environmental detector 90 receives the information via the antenna 100 and the communications circuit 98. This information is transmitted to the processor circuit 104 which generates command signals that are sent to the motion control circuit 106. The motion control circuit 106 uses these control signals to drive a motor that drives the wheels 108 or 110.

U.S. patent application Ser. No. 11/644,755 filed Dec. 22, 2006 and entitled AIR MONITORING SYSTEM AND METHOD, including its entire specification and drawings, is hereby incorporated by reference.

U.S. patent application Ser. No. 12/333,856 filed Dec. 12, 2008, and entitled METHODS AND SYSTEMS FOR ANALYSIS, REPORTING AND DISPLAY OF ENVIRONMENTAL DATA, including its entire specification and drawings, is hereby incorporated by reference.

U.S. patent application Ser. No. 12/333,958 filed Dec. 12, 2008, and entitled METHODS AND SYSTEMS FOR ANALYSIS, REPORTING AND DISPLAY OF ENVIRONMENTAL DATA, including its entire specification and drawings, is hereby incorporated by reference.

U.S. patent application Ser. No. 12/334,061 filed Dec. 12, 2008, and entitled METHODS AND SYSTEMS FOR ANALYSIS, REPORTING AND DISPLAY OF ENVIRONMENTAL DATA, including its entire specification and drawings, is hereby incorporated by reference.

While there have been shown, described and pointed out novel features of the invention as applied to various aspects of the present invention, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

We claim:

1. An environmental measurement system, comprising:
   a base station having a processor; and
   a plurality of environmental detectors located remotely from the base station that measure one or more environmental conditions that are in communication with the base station to send the measured one or more environmental conditions to the base station;
   wherein one of the plurality of environmental detectors is mobile and has a means for determining current position and for reporting it position to the base station; and
   a mobile user display device having a GPS unit that reports time stamped position information to the base station and the base station comparing the time stamped position information to time stamped environmental conditions measured by the plurality of environmental detectors plurality of environmental detectors to determine an exposure level at the mobile user display device.

2. The environmental measurement system of claim 1, comprising a plurality of user displays stations located remotely from the base station that are in communication with the base station and that can display the one or more environmental conditions received from the base station.

3. The environmental measuring system of claim 2, wherein at least one of the plurality of user display stations are mobile.

4. The environmental measuring system of claim 3, wherein each of the plurality of user display stations can selectively display information from any of the plurality of environmental detectors.

5. The environmental measuring system of claim 1, wherein another one or more of the plurality of environmental detectors is mobile and has a means for determining its position and for reporting its position to the base station.

6. The environmental measurement system of claim 4, comprising a plurality of user displays stations located remotely from the base station that are in communication with the base station and that can display the one or more environmental conditions received from the base station.

7. The environmental measuring system of claim 1, wherein at least one of the plurality of user display stations is mobile and has a means for determining its position and for reporting its position to the base station.

8. The environmental measuring system of claim 6, wherein all communications with the base station are wireless communications.

9. Environmental measuring system of claim 1, wherein the mobile environmental detector reports its position to the base station on a periodic basis.

10. The environmental measuring system of claim 1, wherein the mobile environmental detector reports its position to the base station either while moving or stationary.

11. The environmental measuring system of claim 9, wherein the mobile environmental detector reports its position to the base station when queried by the base station.

12. The environmental measuring system of claim 1, wherein the mobile environmental detector reports its position to the base station when queried by the base station, or when an environmental measurement of interest exceeds a preset threshold.

13. The environmental measuring system of claim 4, wherein each of the mobile environmental detectors reports its position to the base station on a periodic basis.

14. The environmental measuring system of claim 4, wherein each of the mobile environmental detectors reports its position to the base station either while moving or stationary.

15. The environmental measuring system of claim 13, wherein each of the mobile environmental detectors reports its position to the base station when queried by the base station.

16. The environmental measuring system of claim 4, wherein each of the mobile environmental detectors reports its position to the base station when queried by the base station.

17. The environmental measuring system of claim 1, comprising a secondary environmental detector located remotely from the base station that measures one or more environmental conditions and that is in communication with one of the plurality of environmental detectors which provides information from the secondary environmental detector to the base station.

18. The environmental measuring system of claim 17, wherein the one of the plurality of environmental detectors that the secondary environmental detector is in communication with is mobile.

19. The environmental measuring system of claim 4, comprising a plurality of secondary environmental detector located remotely from the base station that measures one or more environmental conditions, each of the plurality of secondary environmental detectors being in communication with one of the plurality of environmental detector which provides information from the secondary environmental detector to the base station.

20. The environmental measuring system of claim 1, wherein the means for determining current position is a GPS device.

21. The environmental measuring system of claim 1, wherein the mobile environmental detector is adapted to be worn by a person to act as a personal exposure device for the person.

22. The environmental measuring system of claim 1, wherein the mobile environmental measurement detector is adapted to be mounted on a vehicle.

23. The environmental measuring system of claim 1, wherein the mobile environmental measurement detector is mounted on rollers, wheels, treads; tracks, rails or a cable suspension system, and is robotically controlled.

24. The environmental measuring system of claim 23, wherein the base station issues commands to the mobile environmental measurement detector to control movement of the mobile environmental measurement detector by issuing commands to start or stop the environmental measurements within the system.

25. The environmental measurement system of claim 1, wherein an alarm is sent by the base station to the user display device when the exposure exceeds a limit.

26. The environmental measurement system of claim 1, wherein the base station sends a display of the exposure level to the mobile user display device.

* * * * *